United States Patent [19]

Sendax

[11] Patent Number: 4,693,686
[45] Date of Patent: Sep. 15, 1987

[54] MAGNETIC DENTAL IMPLANT RETENTION SYSTEM

[76] Inventor: Victor I. Sendax, Suite 14B, 30 Central Park South, New York, N.Y. 10019

[21] Appl. No.: 829,725
[22] Filed: Feb. 14, 1986
[51] Int. Cl.⁴ .............................................. A61C 8/00
[52] U.S. Cl. .................................. 433/173; 433/176; 433/189
[58] Field of Search ............... 433/189, 173, 174, 175, 433/176

[56] References Cited

U.S. PATENT DOCUMENTS

| | | | |
|---|---|---|---|
| 783,358 | 2/1905 | Bloom | 433/221 |
| 4,214,366 | 7/1980 | Laban | 433/189 |
| 4,302,189 | 11/1981 | Gillings | 433/189 |
| 4,431,419 | 2/1984 | Portnoy | 433/189 |

Primary Examiner—Robert Peshock

[57] ABSTRACT

A dental prostheses and method of mounting same comprises an implant having an upper neck portion, and a ferromagnetic casted coping comprising a precious metal alloy. A barrier cement layer between the coping and the neck for connecting same and a prosthetic member. A rare earth magnet is fixedly mounted in the prosthetic member at the gum facing side thereof and is coactive with the coping for retaining the prosthetic member in place. The coping is disposed at the crestal gum tissue level at the time of implantation.

5 Claims, 18 Drawing Figures

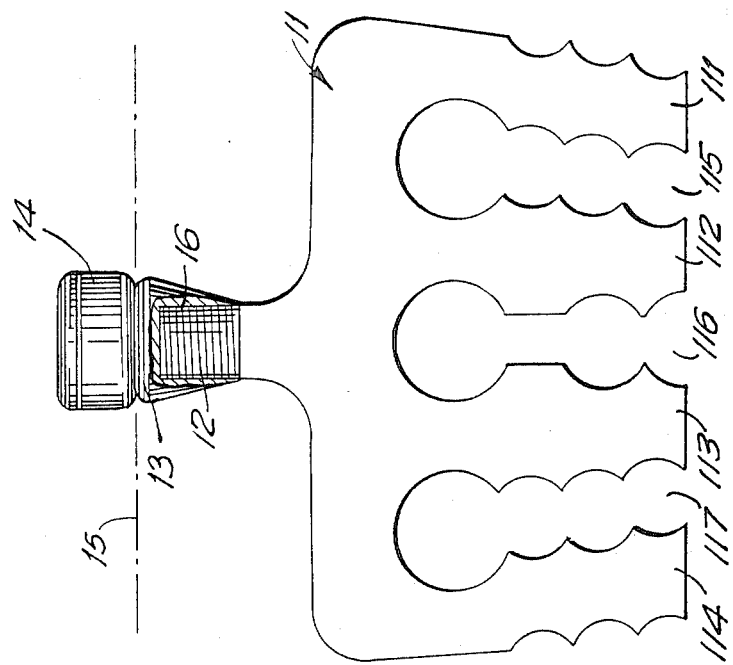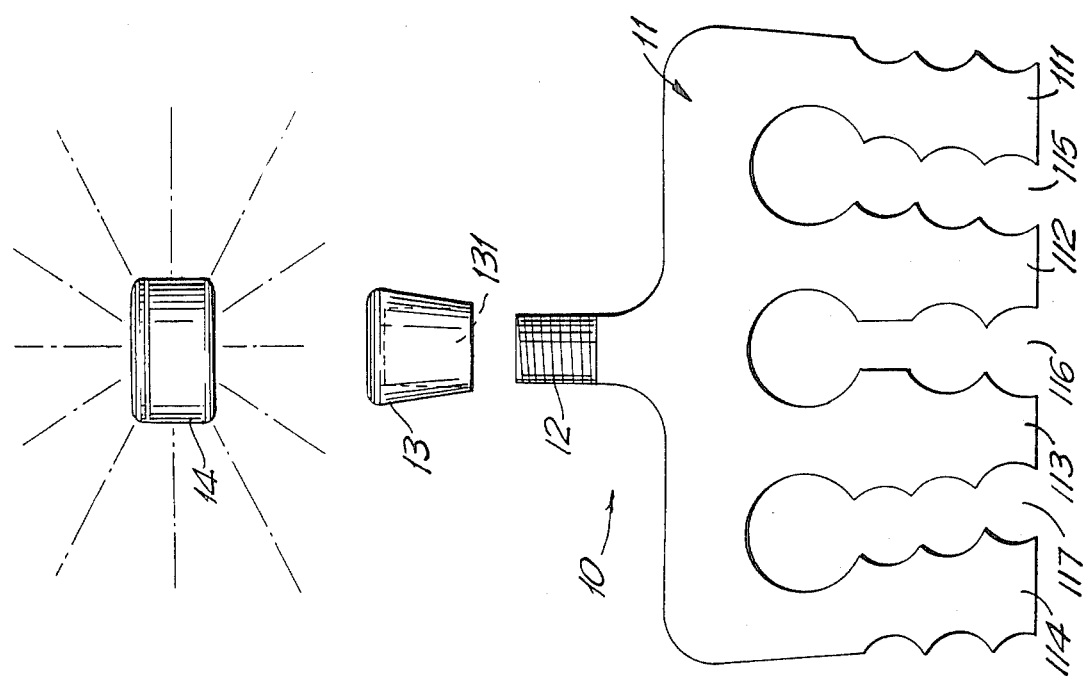

MAGNETIC DENTAL IMPLANT RETENTION SYSTEM

BACKGROUND OF THE INVENTION

The present invention relates to a magnetic dental implant retention system.

SUMMARY OF THE INVENTION

The main object of the present invention is to provide a dental prosthesis and a method of mounting same which overcome the disadvantages of the prior art.

In accordance with the present invention, the mating of a ferromagnetic, precious metal coping to the retentive neck of a dental implant through the use of a barrier cement, permits for the first time, rare earth miniature cobalt magnets to be applied to prosthetic retention systems for dental implants.

The ferromagnetic cast coping is preferably a non-corrosive castable precious metal alloy.

The implant neck extends through the permucosal soft tissue site 1½ mm below the crest of the gingival ridge, providing room for the thickness of the ferromagnetic coping when cemented over this neck, so that the coping emerges as flush with the gingival crestal tissues. This feature of a magnetic-attractive coping residing flush with the ridge crest is important to the method of the invention since it minimizes destructive lateral loading stress on the implant. The barrier cement layer between coping and neck of implant, effectively discourages any dissimilar metal contact with its associated battery potential, and related corrosion morbidity. The cement is preferably zinc oxyphosphate or glass ionomer or resin type. The magnets are rare-earth cobalt-samarium ultraminiature magnets which provide 300 to 700 grams or more of magnetic retentive force, depending on whether magnet is a simple unit, multiple unit or fabricated into a more powerful sandwich assembly.

The prosthetic overdenture or bridge is thus a removable superstructure which retains the magnets on its gum tissue related side. The magnetic retention system also makes possible the often crucial elimination of a full denture palate in upper jaw applications.

The system is also useful for submerged implants, such as (A) Endosseous (in-the-bone) or Endosteal
(B) Subperiosteal (on-the-bone) Full Arch or Unilateral
(C) Endodontic (through natural tooth root into surrounding bone)
(D) Transosseous (or Staple) (through lower jaw when there is a minimum of 9 mm of anterior bone)
(E) Hybrid Combinations of (A), (B), (C) & (D), plus periodontally sound natural teeth having endodontia, but without endostabilizers.

The potential for mixing all forms of implants and natural tooth roots gives the magnetic retention system a versatility unmatched by other existing systems and the potential for an extended useful life for both roots and implants.

The present invention has many advantages associated with it. For example, there is a favorable crown-root ratio or crown-implant ratio since ferro-magnetic coping is fabricated flush with the crest of residual ridge. As a corollary consequence any interdental space, large or small, may be accommodated. Vertical dimension variations and freeway space considerations are readily incorporated into the reconstructive scheme. Further, there is no critical temporization problems since the inventions makes possible a conservative management of periodontal therapy (gingivoplasty and curettage) and simple follow-up to impression-taking consists of painting soft tissues with tincture of benzoin, and saline irrigations. Interim post-coping preparations are temporarily filled with CAVIT or temporary cement between visits.

Moreover, no compromises are necessary on esthetics since minimum bulk of copings and miniature magents minimizes esthetic and contour problems. Additionally, lip and cheek support from the removable prosthesis flanges provide critical plumping where necessary without making the patient unduly conscious of the fact that they are wearing something loose and moveable. The feeling is more akin to the proprioceptive sensation of a fixed bridge than a removable prosthesis, since skidding and instability are virtually eliminated. In many cases where there are sufficient tooth roots and/or implant supports it may be possible to eliminate the palate from maxillary prostheses, adding greatly to the sensation of a fixed, non-gag bridge. Similarly, where there are enough abutment supports, a bulky labial flange may also be eliminated, avoiding the extreme "denture look" where there is already excessive labial alveolar protrusion.

The method is significantly cost-effective as opposed to the onerous unit costs of fixed bridge systems since relatively modest expenses are generated by the precious metal post-copings for both natural roots and implants, along with the cobalt magnets. The only significant expense would relate to the laboratory charges for the removable prosthesis itself, which would be on a par with any conventional denture fabrication. As a consequence, it puts this type of sophisticated prosthetic refinement within the financial reach of patients from all economic strata, with special emphasis on the advanced geriatric patient where funds are often limited and the need is often greatest.

Removal of any one support element is not crucial to the overall success of the magnetic system, and is readily accomplished since the denture is merely taken out of the mouth, the loose root or implant efficiently extracted and the affected site allowed to heal uneventfully under the denture. Wherever there is adequate residual bone a replacement endosseous implant can be inserted and in its submerged state allowed to integrate with the surrounding bone while under the denture.

If insufficient bone is available for an endosseous implant it is still possible to utilize a subperiosteal implant modified to accept the ferro-magnetic copings cemented into place over necks (or uprights) flush with the crestal tissues. Consequently it is possible to readily back off from problems without compromising the basic prosthesis, and replacements via the implant option generate the potential to keep the magnetic retention system consistently viable over the long term.

The method is adaptable to any submergible implant system providing that the implant head is removable following implant placement, or adjustable so that it may be made flush with the crest of the residual ridge. A custom-fitted coping can be fabricated for cementation to any type of implant neck, whether the implant is made of titanium, chrome-cobalt steel, ceramic or pyrolitic carbon. In the special situation involving endodontic stabilizer-implants it is possible to prepare the endodontic implant to fit with a small recessed post preparation so that the resultant ferro-magnetic post-coping functions exactly as it would if it were a natural root post-coping. This endodontic implant application greatly extends the potential for utilizing weak natural tooth roots, providing that they are effectively treated periodontally (as well as endodontically), so that they can be reasonably expected to withstand the magnetic force applied during functional and parafunctional activity. The use of the endodontic implant should markedly enhance the usefulness of relatively weak, loose natural tooth roots with insufficient bony support. In aid of all natural tooth roots and implants that are losing bone it is often desirable to consider the periodontal augmentation of these support elements with the current family of alloplastic augmenting materials such as resorbable-replaceable tricalcium phosphate, non-resorbable hydroxyl-apatite, or a resin, and combined with autogenous bone in some instances. These techniques can extend the useful, functional life of support elements essential to the magnetic retention of this system. Vestibuloplasties and free gingival grafting may also be applied to tooth roots or implant necks penetrating through unattached mucosal tissues to extend the tough zones of attached, keratinized gingiva around such roots and implants.

The invention also has subperiosteal applications since ferro-magnetic copings may be cemented onto permucosal necks of the subperiosteal implant, as well as endosseous applications previously mentioned. This has a particularly important significance when the interdental space is quite extreme as in the case of severely atrophic ridges. In such situations the great superstructure-to-implant ratio produces a very unfavorable lever arm force that can be quite destructive to the subperiosteal implant stability, particularly in the maxilla. The magnetic retention system on the other hand is not subject to the same lever arm problems since the loading forces are only exerted at the ridge crest and, as with endosseous applications, generally in the long axis of the implant and apically directed.

Innumerable situations also present themselves in maxillofacial prosthodontics where the need for additional stability and retention can be critical to the success of the case. Retention of treatable roots and the addition of strategically placed implants along with the use of the ferro-magnetic coping system can combine to produce obturators with the most desirable and comfortable characteristics.

In addition to the combined use of natural tooth roots and implants, further enhancement of the basic magnetic system concept may be realized with the additional utilization of intramucosal inserts in the posterior maxilla where the poor quantity and quality of the residual bone may preclude endosseous and sometimes subperiosteal implant applications. Such a combined retentive scheme could in select cases make possible the elimination of the palatal cover on a full prosthesis, thus giving the patient the relative feeling of a fixed bridge while permitting removal for cleaning and troubleshooting maintenance procedures.

Minimal instrinsic loading on implants and natural roots from this system permits a more routine use of a natural tooth opposing dentition against the prosthesis. A splinted, reconstructed occlusion also presents less of an overly efficient loading hazard, and porcelain or metal occlusions instead of acrylic resin may be considered as reasonable treatment options when applied in conjunction with a reconstruction retained by a ferromagnetic support system. Heretofore, it has been argued that only a complete maxillary denture with acrylic resin teeth is the only conservative opposing occlusion for a subperiosteal implant. With the advent of the ramus extension modification producing increased stability and retention for the implant frame, and the coating of the metal with hydroxyapatite providing a better chance for direct fibrous attachment to the implant framework, the cautionary stance is not quite as valid. In any event the whole question becomes largely academic when considering the magnetic retention approach since *any* well-executed opposing occlusion should then be functionally acceptable.

Another advantage of the invention is that no special training or patient skill is required during the insertion of the prosthesis. This could be particularly crucial for the elderly, handicapped or otherwise medically compromised individual. The magnetic attachments provide an almost automatic repositioning of the case following any displacement during function as well as during voluntary removals, greatly facilitating the initial adjustment period.

The present invention also has a number of applications of which the following are representative examples.

Mixing fixed abutment teeth anteriorly with unilateral (Pterygoid) subperiosteals posteriorly. The fixed total connection of such cases has often resulted in uneven settling of subperiosteal components resulting in broken cement seals, loosening of anterior abutment teeth or rocking of implant posteriorly. With the stress-broken aspect of the magnetic system applied to the posterior subperiosteals the posterior pontics are cantilevered off the anterior abutments and rest passively on the ridge-lapped ferromagnetic copings, attached to the underlying implant frames only via the magnetic flux emanating from the embedded miniature magnets in the pontics. Each component of the system can function independently as required but maintain the stability of the entire system in a gently stress-broken connection. Large interdental spaces will not produce unfavorable implant-to-superstructure ratios, nor will the presence of fixed prostheses or splinted natural teeth be potentially destructive in the opposing arch due to a heavier biting efficiency. Bruxism and stressful clenching of the jaws should also be much less significant as destructive parafunctional forces since lateral loading is virtually eliminated in the magnetic system.

Branemark osseointegrated implants which function essentially as ankylosed abutment fixtures also should match up easily in this system application since there is no direct connection from the anterior fixtures to posterior subperiosteal or endosseous implants with relatively more mobile fibro-osseous suspensory ligaments. Thus, Branemark's original cautionary remarks about not connecting natural tooth abutments to the osseointegrated fixtures does not appear to have any pertinence in regard to the non-mechanically connected, but in fact uniquely stress-broken magnetic system, thus making it possible to readily combine elements while greatly expanding the original osseointegrated concept and eliminating some of the bio-mechanical loading criticisms leveled against the Branemark approach (e.g. unfavorable superstructure-to-implant ratio and excessive cantilever extensions).

Subperiosteal and natural tooth root combinations should be easily managed since all elements are essentially independent from one another and even a few isolated roots (with or without endodontic stabilizers)

can be interspersed between the usual subperiosteal abutment necks to give added load distribution from the magnet/coping combinations, and an opportunity to salvage a few remaining roots even when the decision is for a subperiosteal implant. If they later fail then the basic subperiosteal is not compromised if they must be extracted, and in fact could contribute to the subperiosteal's early survival period even when the tooth roots themselves might be subsequently lost.

Other combination applications include subperiosteal and endosseous implants and natural tooth roots (with or without endostabilizers), endosseous implant with magnetic coping under pontic holding magnet for Maryland Bridge for maximal stabilization of bonded retainer elements, and transosseous or staple implant with two ferromagnetic copings cemented over two threaded pins cut flush with crestal gum tissue to minimize anteroposterior rock and destructive loading of implant by overdenture.

These and other advantages and features of the present invention will be better seen from the attached description with reference to the accompanying drawings wherein:

BRIEF DESCRIPTION OF THE DRAWINGS

FIG. 1A and FIG. 1B show an exploaded view and a simple view of an endosseous implant in accordance with the present invention;

DETAILED DESCRIPTION OF THE INVENTION

Figure 2A:
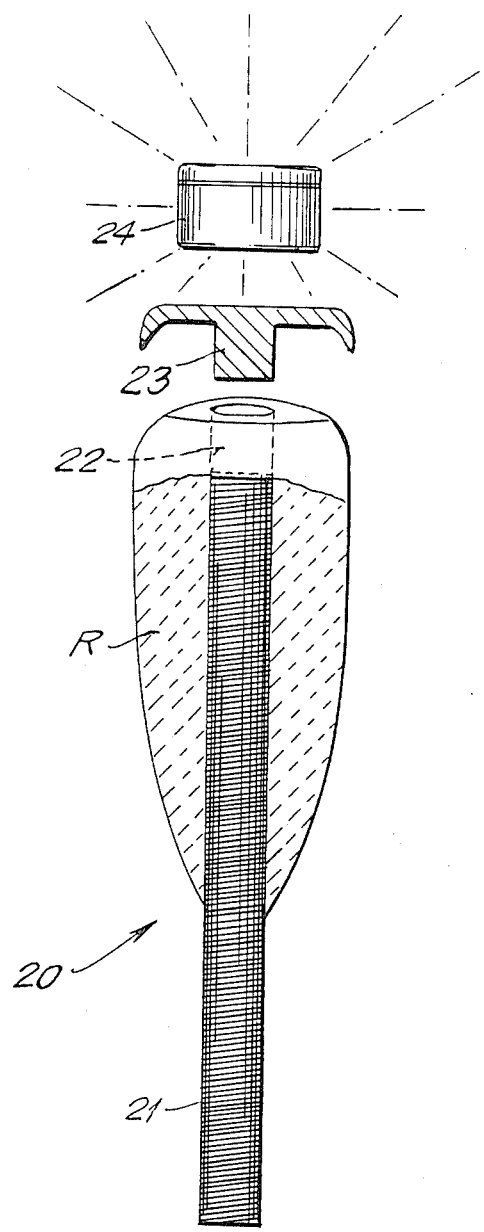
FIGS. 2A and 2B show an exploaded and an assembled view of an endodontic stabilizer implant in accordance with the present invention.

Referring now to FIGS. 1A and 1B, an endosseous or endosteal implant is shown. The implant includes an implant member 11 having a plurality of tines 111, 112, 113, 114 forming recesses 115, 116, 117 in which bone can be situated when the implant is placed in situ. The implant member 11 further comprises a knurled neck portion 12. The device further comprises a ferromagnetic coping 13 having a recess 131 therein and a magnet 14 comprising a rare earth metal. When placed in the mouth of a patient, the implant member 11 is placed so that the neck portion 12 is below the gum tissue level 15 so that when the coping is seated and cemented on the implant neck by cement layer 16, the top of the coping will be at the crestal gum tissue level 15 as shown. The magnet 14 can then coact with the coping and retain a dental prostheses in place as will be shown hereinafter.

Figure 2B:
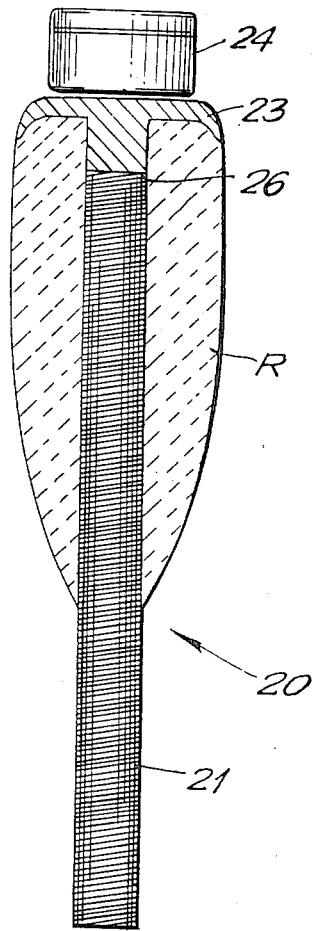
Figure 3:
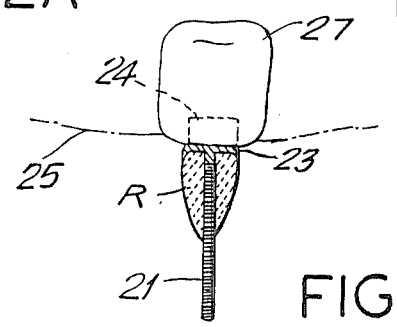
FIG. 3 shows the implant of FIGS. 2A and 2B in situ.

FIGS. 2A and 2B show an endodontic stabilizer implant 20. The stabilizer implant comprises implant member 21 which is knurled along its entire length and which is implanted through a tooth root R as shown. When the implant member 21 is placed in the tooth root R, a countersunk post receptacle 22 is provided for which receives the post of coping 23 which is cemented in place by a cement layer 26. As shown in FIG. 3 the coping is disposed so that the top thereof is at the crestal gum tissue level 25. Magnet 24 is conveniently placed on the gum facing surface of a prosthetic member 27 so it can coact with the coping 23 to maintain the prosthetic member 27 in place.

Figure 4:
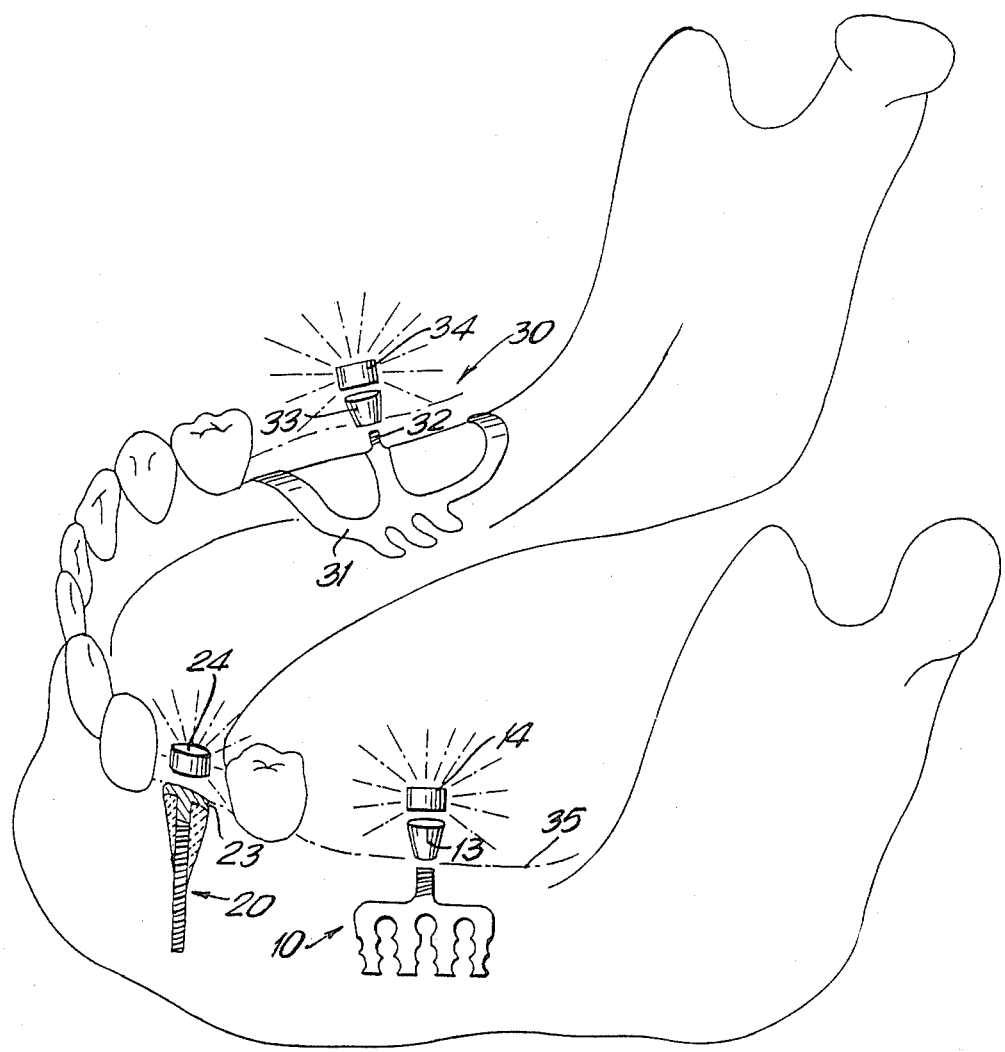
FIG. 4 shows a lower jaw with an endodontic implant, an endosseous implant and a subperiosteal implant.

FIG. 4 shows the lower jaw with an endodontic stabilizer implant 20, and endosseous implant 10 and a lower subperiosteal implant 30 which includes an implant member 31, a knurled neck portion 32, a coping 33 and magnet 34 similar to devices 10 and 20 described hereinbefore. The crestal gum tissue level 35 is also indicated for the lower jaw.

Figure 5:
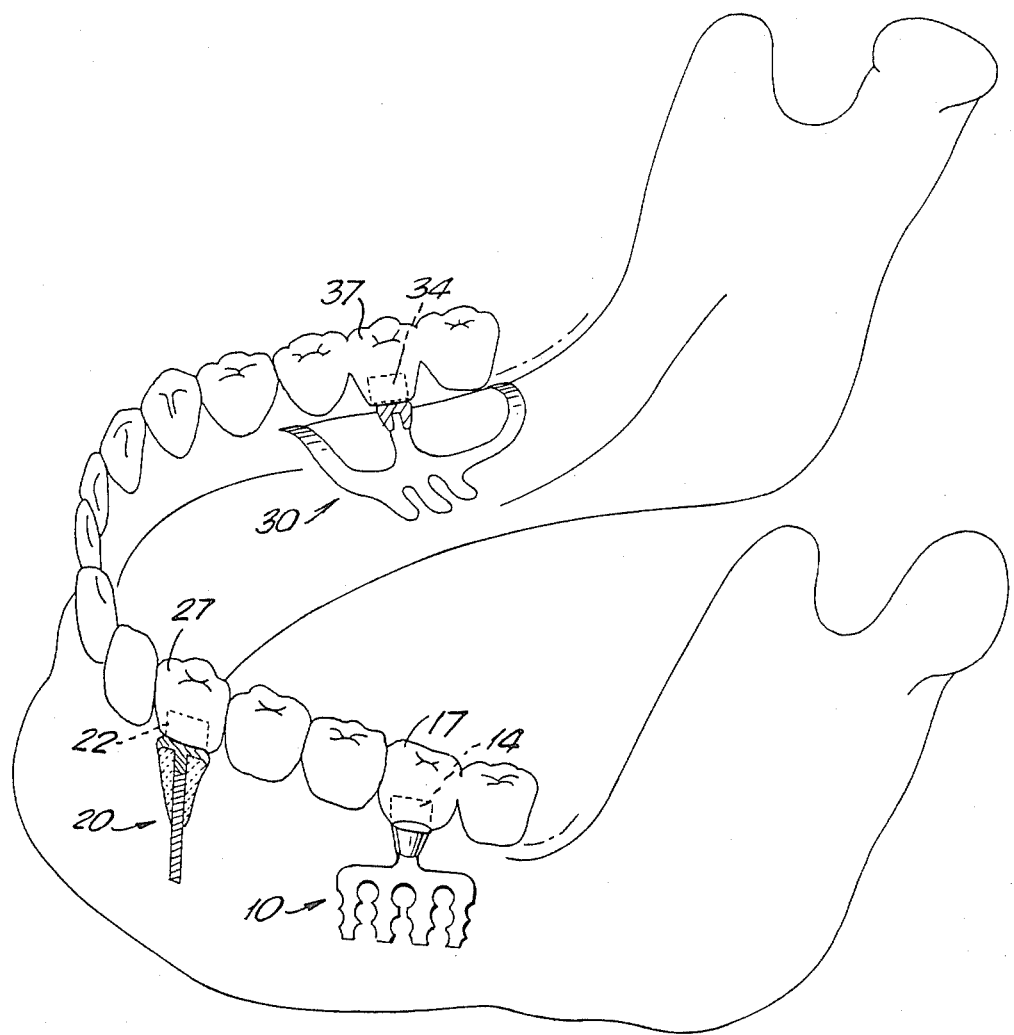
FIG. 5 shows the lower jaw of FIG. 4 with the prostheses in place.

As shown in FIG. 5, these implants are used to hold dental prostheses 17, 27 and 37 in place by means of the magnets 14, 24 and 34 being disposed at the tissue facing side of the prostheses members and coacting with copings 13, 23 and 33 which are disposed at the crestal gum tissue level 35.

Figure 13:
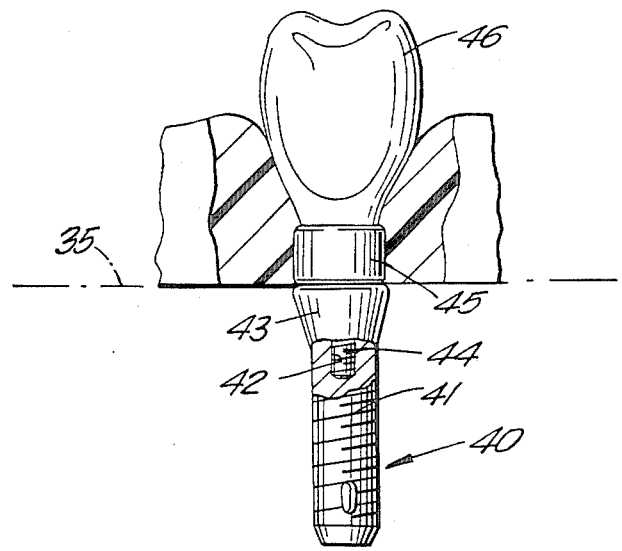
FIG. 13 shows a partial sectional view of a Branemark implant modified in accordance with the invention.

FIG. 13 shows a modified Branemark implant 40 having a threaded implant member 41 which terminates in an internally threaded recess 42 below the gum tissue level 35. This construction differs from the standard Branemark implant in that the conventional Branemark implant has the member or abutment coping (protruding upwardly through the gum level and into the artificial tooth 46.

In accordance with the present invention, a coping 43 has a threaded extension 44 which is received into recess 42 and into which also cement is added to ensure connection. The top of coping 43 is disposed at or around the gum tissue level 35. The artificial tooth 46 is connected by adhesive such as an acrylic resin to magnet 45 which engages coping 43 as in the previous embodiments.

Figure 14:
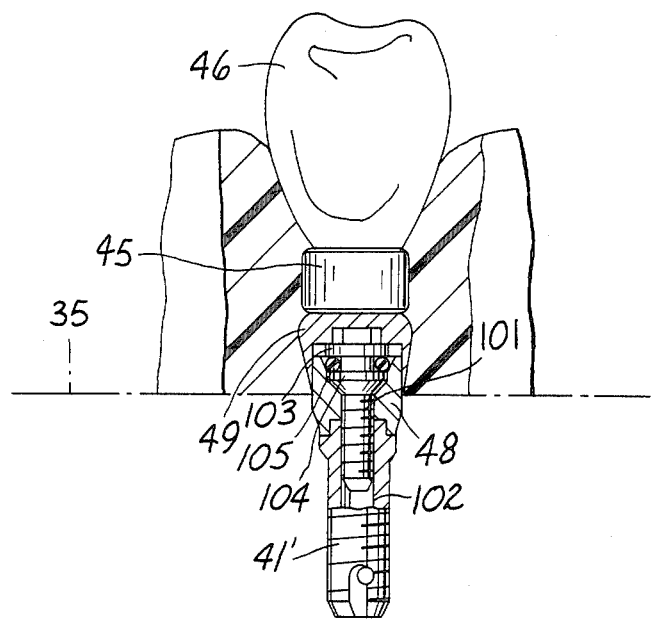
FIGS. 14-16 show section of modified embodiments of FIG. 13.

FIG. 14 shows a Branemark osseointegrated implant modified, in accordance with the invention to include member 41', a titanium abutment 48 which is about 2 to 4 mm high, a ferro-magnetic coping 49 cemented to abutment 48. The magnet 45 and prosthetic tooth 46 in the prosthetic superstructure are the same as in FIG. 13.

In the modified Branemark osseointegrated implant depicted in FIG. 14, a screw with a hex nut head 101 connects coping 49 to the abutment 48 and the implant 102. The implant 102 has screw threads which couple with the screw threads on screw 101. Between flanges 103 and 104 on screw 101 is an O-ring 105.

Figure 15:
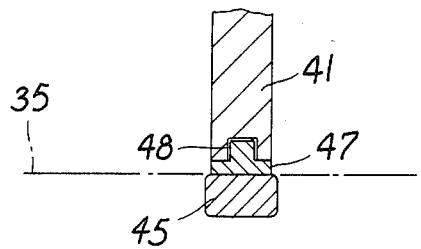
Figure 16:
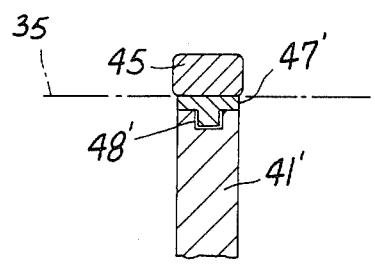

In FIGS. 15 and 16, for maxillary and mandibular subperiostal implants respectively, the embodiment of FIG. 13 is modified by the use of ferromagnetic inlay 47, 47' which is about 2 mm in height at the base is cemented into member 41, 41' by cement 48, 48'.

Figure 6:
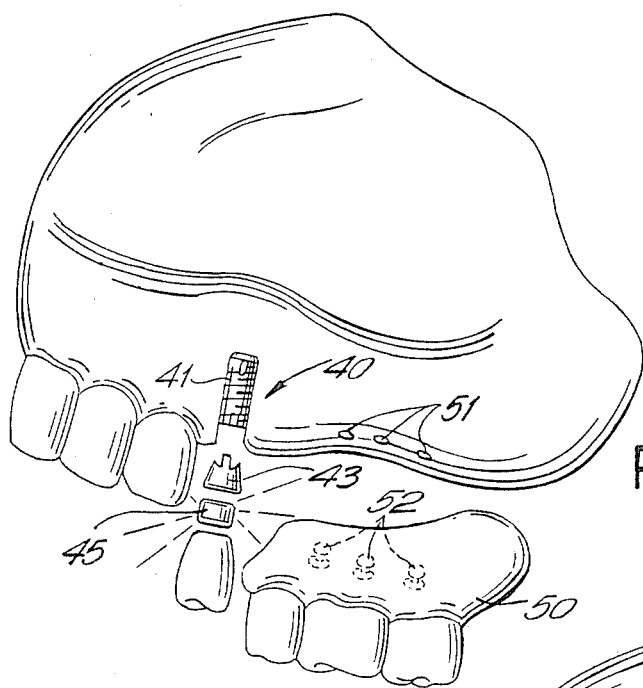
FIG. 6 shows an upper jaw with an exploded view of hybrid osseointegrated and intra-mucosal implants.
Figure 7:
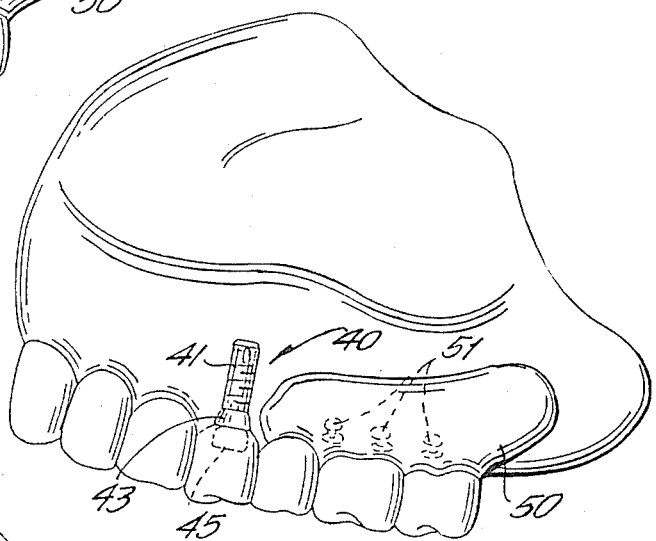
FIG. 7 shows a cutaway view of the implants of FIG. 6 in place.
Figure 8:
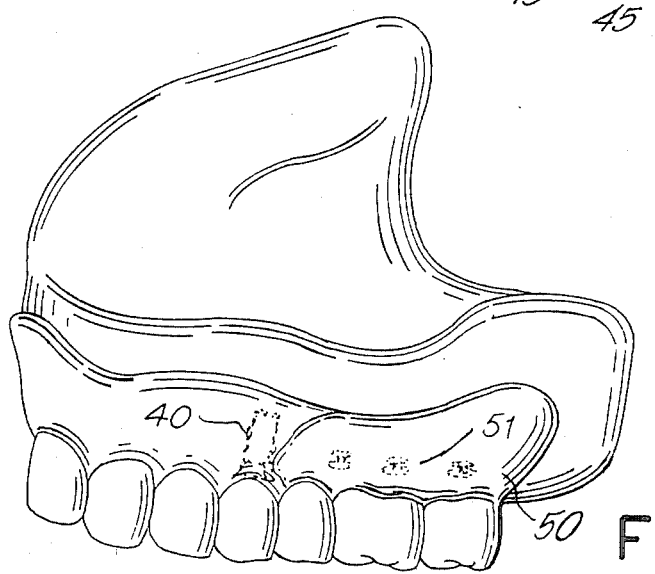
FIG. 8 shows the final appearance of the upper jaw with the implants of FIG. 6.

The use of the modified Branemark implant is shown in FIGS. 6-8. As shown therein, the implant 40 is disposed next to a hybrid intra-mucosal insert 50 into the upper jaw of a patient. The insert 50 is connected in a conventional manner with "buttons" 52 which are received into holes 51 in the gum of the user. FIGS. 7 and 8 show how the present invention is compatible with prior art techniques in order to obtain a hybrid of osseointegrated implants and intra-mucosal inserts.

Figure 9:
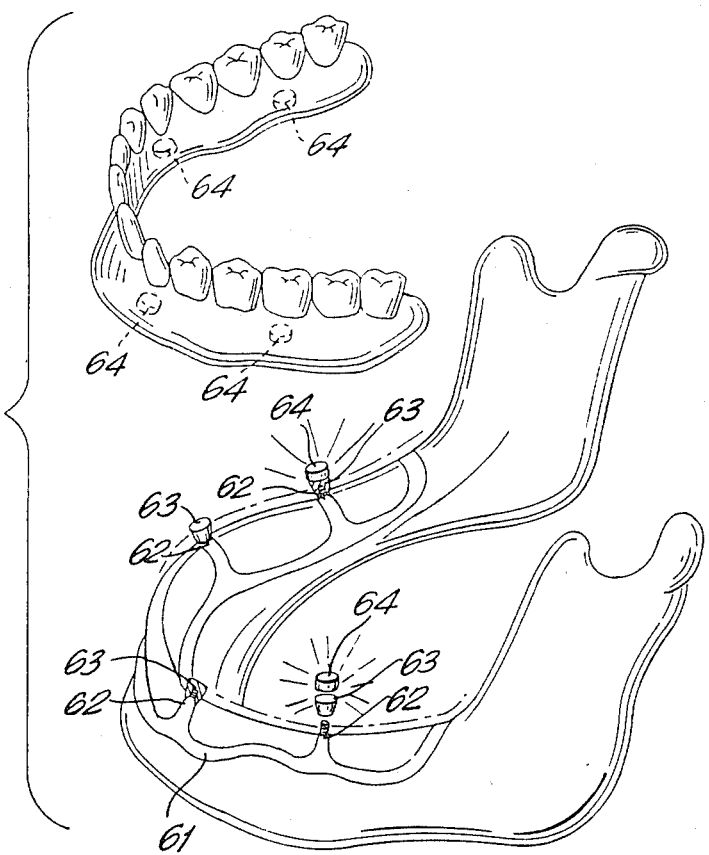
FIG. 9 shows an exploded view of a subperiosteal implant for a lower jaw in accordance with the invention.
Figure 10:
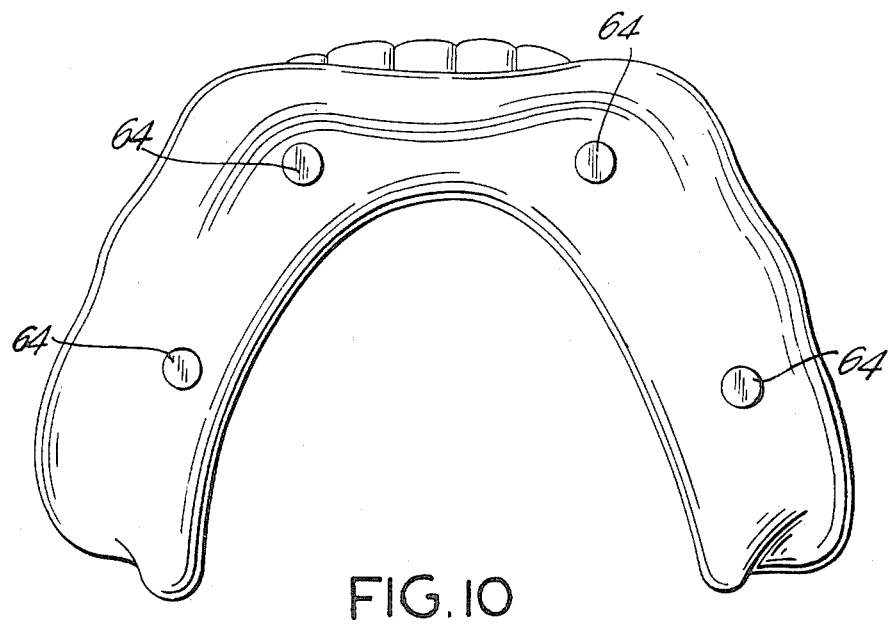
FIG. 10 shows a bottom view of the insert of FIG. 9.

FIGS. 9 and 10 show a lower subperiosteal implant wherein an implant member 61 similar to that labeled 31 in FIG. 4 but comprising four knurled neck portions 62, four copings 63 and four implanted magnets 34 which are used to hold an entire upper bridge in place.

Figure 11:
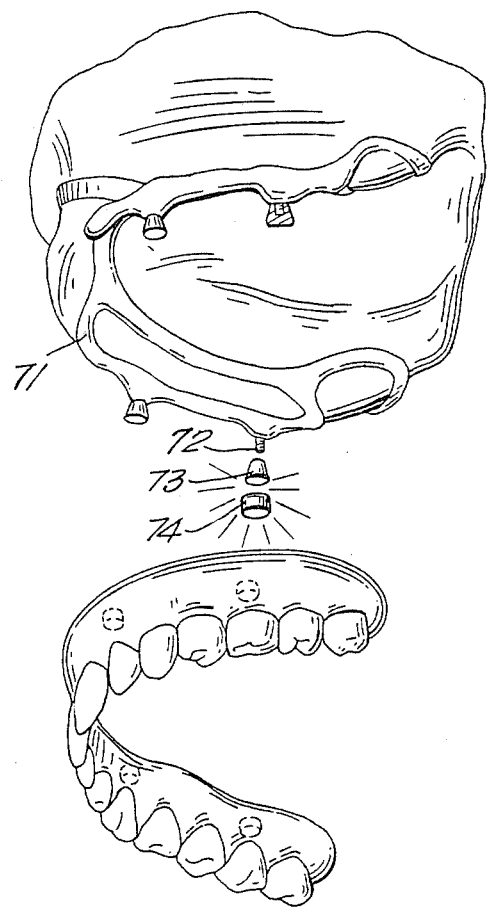
FIG. 11 shows an exploded view of a subperiosteal implant for an upper jaw in accordance with the invention.

FIG. 11 shows the same construction 71 for an upper subperiosteal implant and includes neck portions 72, copings 73 and magnets 74.

Figure 12:
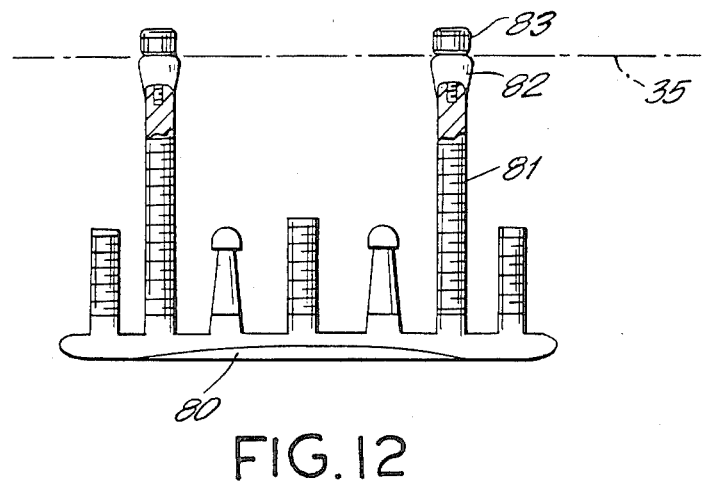
FIG. 12 shows a partial sectional view of a mandibular lower jaw staple implant modified in accordance with the present invention.

FIG. 12 shows a mandibular lower jaw staple which conventional is used to be fitted into a patient's jaw through an extra oral incision under the jaw to support prosthetic teeth. The staple 80 has been modified in accordance with the present invention to shorten the implant members 81 so that rather than normally extending upwardly past the gum tissue level 35, the implant members 81 along with copings 82 are disposed right at the level of the gum tissue 35. Magnets 83 are then inserted into the artificial teeth which are to be held in place.

In accordance with the invention, the ferro-magnetic alloy for the copings is preferably palladium/cobalt with more than 50% palladium content (making it essentially a semi-precious material), susceptible to magnetism, and resistant to corrosion. It is a castable and solderable, biocompatable alloy which contains no toxic or allergenic elements. It is used for cast metal copings made from intra-oral impressions which are then cemented over the implant posts or necks. These copings are made so that their top (intra-oral) surfaces are generally flush with the crestal gum tissues, though they may end up slightly higher or lower than the actual gum tissue without problems. The diameter of the top of the coping surface is approximately 4.5 mm. The height of the coping is approximately 4 mm.

Alternately, stainless steel prefabricated keepers may be used instead of ferro-magnetic cast copings in some root implant and subperiosteal applications. In such applications keepers are cemented into the recessed permucosal posts or necks of the implants most typically used with four posts for adequate retention and load distribution and balance.

Four types of currently available dental cements may be used to cement the cast copings or prefabricated keepers:

1. Zinc Oxyphosphate
2. Resin
3. Glass Ionomer
4. Polycarboxylate

However, any durable dental cement would be acceptable for this purpose. The need for some form of cementation to connect the keeper metal to the underlying implant is important. Since the keeper and the implant are dissimilar metals and any direct contact between these elements without an intervening cement barrier would inject the risk of a battery action (with the saliva as the electrolyte) and potential corrosion of the implant. While the degree of such corrosive potential over long-term time spans intraorally is unclear, it is not a permissable risk if one is trying to avoid all plausible implant rejection problems.

The invention preferably utilizes rare-earth cobalt-samarium magnets with magnetic strengths varying from 250 to 750 or more grams of retentive force. Surface diameters of the magnets range from 4 to 5 mm. Configurations may vary from plain, uncompanded types to more complex sandwich assembly types which are designed to provide higher levels of retentive force.

This system represents the first time that a magnetic retention system has been devised for dental implants of all types currently available, permitting the hybridization and reconciliation of all these diverse types. Furthermore, the concept of cementing the keeper component to the underlying implant (as compared to any direct screw-in metal to metal contact or soldering or welding) eliminates effectively any potential criticism involving dissimilar metal corrosion. It also makes the system infinitely flexible for in-the-mouth application at the time of insertion and during follow-ups over the ensuing years.

It is the adapting of the principle of magnetic retention to the entire spectrum of contemporary implantology that lies at the heart of this invention. It offers the prospect of a basically simpler, straightforward technique that is at the same time cost effective and predictable to millions of denture users who face otherwise bleak alternatives. This is especially true with the increasing age of the population at large and a pressing need to improve the quality of existence for this burgeoning geriatric component.

It will be appreciated that the instant specification and claims are set forth by way of illustration and not limitation, and that various modifications and changes may be made without departing from the spirit and scope of the present invention.

What is claimed is:

1. A dental prosthesis comprising:
   a. an implant having an upper neck portion;
   b. a ferromagnetic casted coping comprising a precious metal alloy;
   c. a prosthetic member having a gum facing side;
   d. a rare-earth magnet fixedly mounted in the prosthetic member at the gum facing side and coactive with the coping for retaining the prosthetic member in place;
   e. a titanium abutment having a height of 2 to 4 mm, the abutment disposed between the coping and the implant, the abutment being cemented to the coping; and
   f. a screw means disposed within the abutment and implant for connecting the abutment and implant to the coping.

2. A dental prosthesis according to claim 1, wherein said screw means is a screw having a hex nut shaped top portion adjacent to the coping and said screw having threads corresponding to threads in the abutment.

3. A dental prosthesis according to claim 2, wherein adjacent to said hex nut top portion of the screw is a first flange disposed on the screw and adjacent to said first flange is an O-ring which is held in place between said first flange and a second flange disposed on the screw.

4. A method for mounting a dental prosthesis in a patient, comprising:
   a. inserting an implant in the gum having a neck portion the crest of the gingival ridge;

b. attaching a cast ferromagnetic coping to the implant by a barrier cement layer therebetween, with the top of the coping flush with the ginginal crestal tissues;

c. placing a prosthetic member with a rare-earth magnetic fixed at the gum facing side thereof on the coping, whereby the magnetic and coping coact to retain the prosthetic member in place.

5. The dental prosthesis according to claim 1, wherein the magnet comprises at least one component comprising rare earth cobalt-samarium and having a magnetic retentive force in the range of 300 to 700 grams.

* * * * *

UNITED STATES PATENT AND TRADEMARK OFFICE
CERTIFICATE OF CORRECTION

PATENT NO. : 4,693,686

DATED : September 15, 1987

INVENTOR(S) : Victor I. Sendax

It is certified that error appears in the above-identified patent and that said Letters Patent is hereby corrected as shown below:

Title Page, under "Primary Examiner"   Insert --Attorney, Agent or Firm SPRUNG HORN KRAMER & WOODS--

Signed and Sealed this

Twelfth Day of July, 1988

Attest:

DONALD J. QUIGG

*Attesting Officer*   *Commissioner of Patents and Trademarks*